United States Patent
Chen et al.

(10) Patent No.: US 11,940,388 B2
(45) Date of Patent: Mar. 26, 2024

(54) METHOD FOR IMPROVING USABILITY AND ACCURACY FOR PHYSIOLOGICAL MEASUREMENT

(71) Applicant: iXensor CO., LTD., Taipei (TW)

(72) Inventors: Yenyu Chen, Taipei (TW); An Cheng Chang, Taipei (TW); Tai I Chen, Taipei (TW); Su Tung Yang, Taipei (TW); Chih Jung Hsu, Taipei (TW); Chun Cheng Lin, Taipei (TW); Min Han Wang, Taipei (TW); Shih Hao Chiu, Taipei (TW)

(73) Assignee: IXENSOR CO., LTD. (TW)

( * ) Notice: Subject to any disclaimer, the term of this patent is extended or adjusted under 35 U.S.C. 154(b) by 548 days.

(21) Appl. No.: 16/494,313

(22) PCT Filed: Mar. 16, 2018

(86) PCT No.: PCT/CN2018/079317
§ 371 (c)(1),
(2) Date: Sep. 16, 2019

(87) PCT Pub. No.: WO2018/166533
PCT Pub. Date: Sep. 20, 2018

(65) Prior Publication Data
US 2020/0080942 A1  Mar. 12, 2020

Related U.S. Application Data

(60) Provisional application No. 62/521,457, filed on Jun. 18, 2017, provisional application No. 62/487,486, (Continued)

(51) Int. Cl.
G01N 21/84 (2006.01)
A61B 5/145 (2006.01)
(Continued)

(52) U.S. Cl.
CPC ..... *G01N 21/8483* (2013.01); *A61B 5/14532* (2013.01); *A61B 5/150358* (2013.01); (Continued)

(58) Field of Classification Search
None
See application file for complete search history.

(56) References Cited

U.S. PATENT DOCUMENTS

2012/0140319 A1\*  6/2012  Moribe ................. G06F 3/0425
                                                                    359/460
2013/0273528 A1  10/2013  Ehrenkranz
(Continued)

FOREIGN PATENT DOCUMENTS

CN  102095497 A  6/2011
CN  102692410 A  9/2012
(Continued)

OTHER PUBLICATIONS

Notification of Reason for Refusal from Korean Intellectual Property Office, dated Jul. 27, 2020.
(Continued)

*Primary Examiner* — Lore R Jarrett
(74) *Attorney, Agent, or Firm* — SU IP CONSULTING

(57) ABSTRACT

Example methods are provided to improve placement of an adaptor (210,220) to a mobile computing device (100) to measure a test strip (221) coupled to the adaptor (220) with a camera (104) and a screen (108) on a face of the mobile computing device (100). The method may include displaying a light area on a first portion of the screen (108). The first portion may be adjacent to the camera (104). The light area and the camera (104) may be aligned with a key area of the test strip (221) so that the camera (104) is configured to capture an image of the key area. The method may further include providing first guiding information for a user to
(Continued)

place the adaptor (210,220) to the mobile computing device (100) according to a position of the light area on the screen (108).

9 Claims, 7 Drawing Sheets

Related U.S. Application Data filed on Apr. 20, 2017, provisional application No. 62/472,585, filed on Mar. 17, 2017.

(51) Int. Cl.
  *A61B 5/15* (2006.01)
  *A61B 5/157* (2006.01)
(52) U.S. Cl.
  CPC ...... *A61B 5/157* (2013.01); *A61B 2562/0295* (2013.01); *G01N 2201/0221* (2013.01)

(56) References Cited

U.S. PATENT DOCUMENTS

| | | | |
|---|---|---|---|
| 2014/0072189 A1 | 3/2014 | Jena et al. | |
| 2014/0170757 A1 | 6/2014 | Tsai et al. | |
| 2015/0233898 A1 | 8/2015 | Chen et al. | |

FOREIGN PATENT DOCUMENTS

| | | | |
|---|---|---|---|
| CN | 103002795 | A | 3/2013 |
| CN | 103091486 | A | 5/2013 |
| CN | 103649731 | A | 3/2014 |
| CN | 105164514 | A1 | 12/2015 |
| CN | 105190291 | A | 12/2015 |
| GB | 2483482 | A | 3/2012 |
| JP | 2005-030983 | A | 2/2005 |
| JP | 2010-250675 | A | 11/2010 |
| JP | 2011-252851 | A | 12/2011 |
| JP | 2015-158519 | A | 9/2015 |
| JP | P2015-180862 | A | 10/2015 |
| JP | 2015-533211 | A | 11/2015 |
| JP | 2016-503880 | A | 2/2016 |
| JP | 2016-173796 | A | 9/2016 |
| KR | 101257676 | B1 | 5/2013 |
| KR | 1020160125715 | A | 11/2016 |
| TW | 201631310 | A | 9/2016 |
| TW | 201840293 | A | 11/2018 |
| WO | 2013162631 | A1 | 10/2013 |
| WO | 2014025415 | A2 | 2/2014 |
| WO | 2014115666 | A1 | 7/2014 |
| WO | 2018166533 | A1 | 9/2018 |
| WO | 2012131386 | A1 | 10/2020 |

OTHER PUBLICATIONS

International Search Report and Written Opinion of the International Searching Authority, International application No. PCT/CN2018/079317, dated Jun. 15, 2018.

The Extended European Search Report, application No. 18766964.3-1115, dated Nov. 24, 2020.

* cited by examiner

METHOD FOR IMPROVING USABILITY AND ACCURACY FOR PHYSIOLOGICAL MEASUREMENT

CROSS-REFERENCE TO RELATED APPLICATIONS

The present application is a U.S. national stage filing under 35 U.S.C. § 371 of International Application No. PCT/CN2018/079317, filed Mar. 16, 2018, which claims the benefit of U.S. Provisional Application No. 62/472,585 filed Mar. 17, 2017, U.S. Provisional Application No. 62/487,486 filed Apr. 20, 2017 and U.S. Provisional Application No. 62/521,457 filed Jun. 18, 2017. The International Application and the U.S. Provisional Applications above are incorporated by reference in their entirety.

BACKGROUND

In recent years, in-vitro diagnosis (IVD) devices, especially blood glucose meters, have gained wide adoption among patients with chronic diseases. In order to take measurements, patients usually have to carry standalone IVD devices with them at all times.

For typical IVD measurements, test strips consisting enzyme and reagent are used. Upon receiving the sample fluid, the test strip's characteristics, such as electrical impedance or color, change according to the concentration of the targeted analyte, such as blood glucose or blood cholesterol.

Optochemistry-based IVD systems usually comprises test strips that change color according to the concentration of analyte received, specific light sources that illuminate on strips, optical sensors that detect scattering light, and light-isolating cases. However, these traditional IVD devices do not support any mechanism to verify or calibrate their operating states before or while analyzing the test strips, resulting in inconsistent and sometimes unreliable test results.

SUMMARY

In examples of the present disclosure, methods are provided to improve placement of an adaptor to a mobile computing device to measure a test strip coupled to the adaptor with a camera and a screen on a face of the mobile computing device. The methods may include displaying a light area on a first portion of the screen. The first portion may be adjacent to the camera. The light area and the camera may be aligned with a key area of the test strip so that the camera is configured to capture an image of the key area. The methods may further include providing first guiding information for a user to place the adaptor to the mobile computing device according to a position of the light area on the screen In examples of the present disclosure, methods are provided to improve measurement of an analyte with a mobile computing device coupled to an adaptor configured to receive a test strip having a key area containing a reagent that reacts with the analyte. The methods may include detecting a first position of the mobile computing device prior to analyzing an image of the key area captured by a camera of the mobile computing device. In response to the first position being substantially horizontal, the methods may include performing an analysis on the image of the key area. In response to the first position exceeding a first threshold from being substantially horizontal, the methods may include providing first guiding information for a user to adjust the first position.

BRIEF DESCRIPTION OF THE DRAWINGS

The foregoing and other features of the present disclosure will become more fully apparent from the following description and appended claims, taken in conjunction with the accompanying drawings. These drawings depict only several embodiments in accordance with the disclosure and are therefore not to be considered limiting of its scope. The disclosure will be described with additional specificity and detail through use of the accompanying drawings.

DETAILED DESCRIPTION

Figure 1:
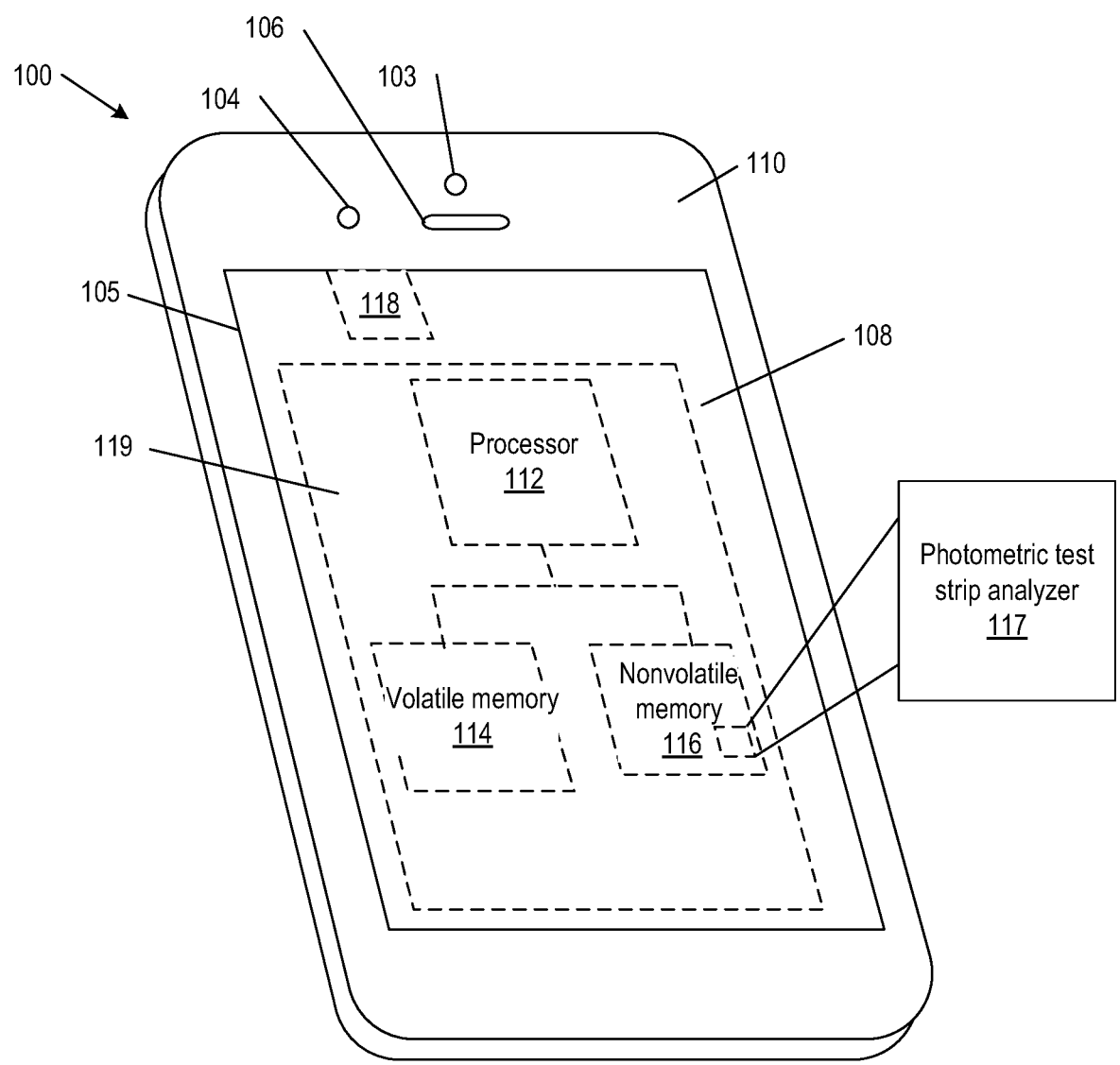
FIG. 1 illustrates a perspective view of mobile computing device 100, according to some embodiments of the present disclosure.

In the following detailed description, reference is made to the accompanying drawings, which form a part hereof. In the drawings, similar symbols typically identify similar components and same numerals typically identify same components, unless context dictates otherwise. The illustrative embodiments described in the detailed description and drawings are not meant to be limiting. Other embodiments may be utilized, and other changes may be made, without departing from the spirit or scope of the subject matter presented here. It will be readily understood that the aspects of the present disclosure, as generally described herein, and illustrated in the drawings, can be arranged, substituted, combined, and designed in a wide variety of different configurations, all of which are explicitly contemplated herein.

FIG. 1 illustrates a perspective view of mobile computing device 100, according to some embodiments of the present disclosure. Mobile computing device 100 has proximity sensor 103, camera 104, ear speaker 106, and screen 108 on face 110 (e.g., a front face) of mobile computing device 100. On face 110, proximity sensor 103 and camera 104 may be located adjacent to each other. Ear speaker 106 may have the form of a hole (as shown) or a protrusion above face 110 (not shown). Mobile computing device 100 includes processor 112, volatile memory 114 and nonvolatile memory 116. Nonvolatile memory 116 stores the code for photometric test strip analyzer 117. Mobile computing device 100 may be a mobile phone, a tablet computer, or a laptop computer.

In some embodiments, screen 108 may include light source area 118 and user interface area 119. Light source area 118 is configured to emit light to enter an adaptor (e.g., a mobile computing device adaptor, a test strip adaptor or an integrated adaptor for the mobile computing device and the test strip) coupled to mobile computing device 100. The light emitted by light source area 118 is configured to illuminate a key area of a test strip (e.g., reaction area of test strip) received in or coupled to the adaptor. Camera 104 is configured to capture an image of the key area of the test strip illuminated by lights emitted from light source area 118 and passed through, scattered or reflected from the key area of the test strip. Light source area 118 and camera 104 are aligned with the key area of the test strip. Photometric test strip analyzer 117 is configured to analyze the captured image to obtain information associated with an analyte on the test strip.

Figure 2:
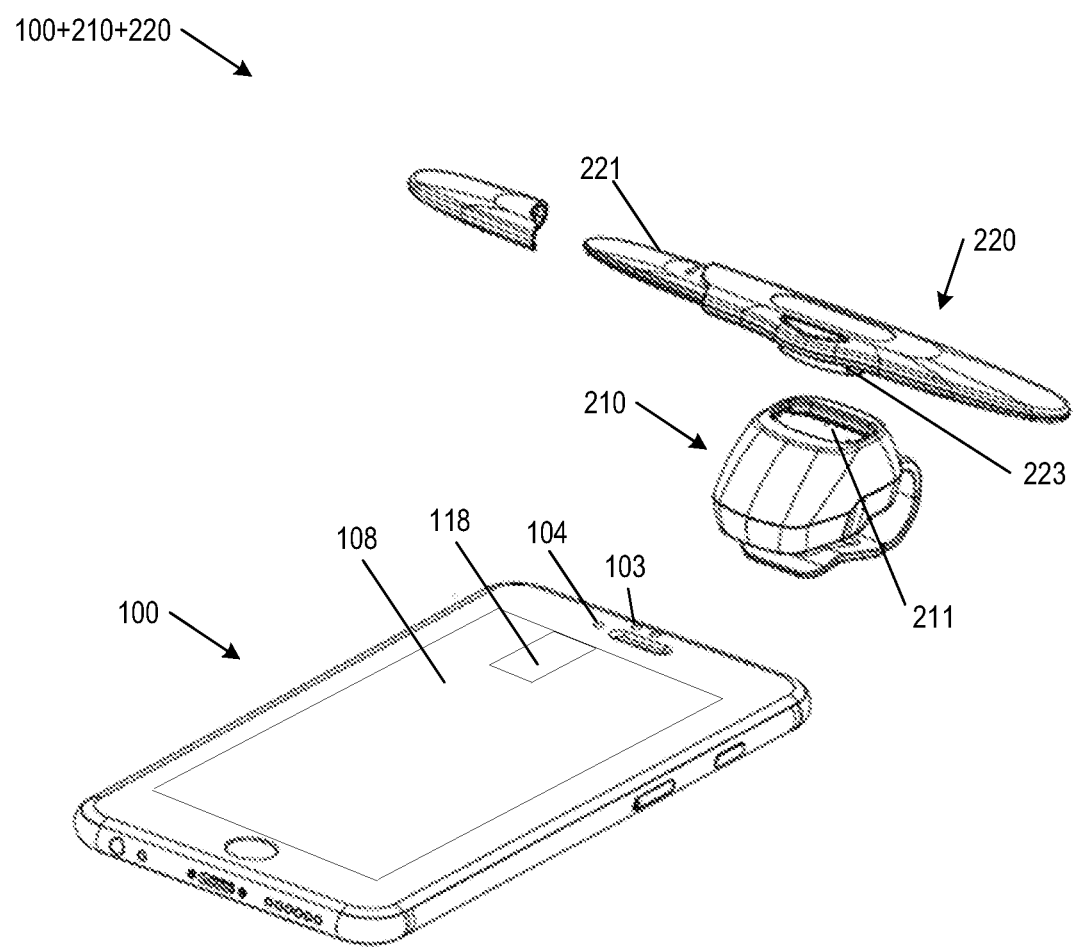
FIG. 2 illustrates an exploded top perspective view of mobile computing device 100, mobile computing device adaptor 210 and test strip adaptor 220, according to some embodiments of the present disclosure.

FIG. 2 illustrates an exploded top perspective view of mobile computing device 100, mobile computing device adaptor 210 and test strip adaptor 220, according to some embodiments of the present disclosure. In some embodiments, mobile computing device adaptor 210 is configured to couple to mobile computing device 100 and test strip adaptor 220 is configured to couple to mobile computing device adaptor 210. In some embodiments, mobile computing device adaptor 120 and test strip adaptor 220 may be integrated to form an integrated adaptor.

In some embodiments, test strip adaptor 220 is configured to receive test strip 221. Test strip 221 may include a key area (e.g., reaction area). The reaction area contains reagents that can react with an analyte (e.g., glucose) in a specimen sample (e.g., blood sample) that is in contact with test strip 221. When the specimen sample reaches the reaction area, the reaction area changes color according to a characteristic of the analyte (e.g., glucose level in blood).

In some embodiments, after test strip 221 is fully inserted into test strip adaptor 220, the location of the reaction area of test strip 221 corresponds to test strip adaptor opening 223. Test strip adaptor 220 may be coupled to mobile computing device adaptor 210. In some embodiments, test strip adaptor opening 223 may correspond to and optically communicate with top opening 211 of mobile computing device adaptor 210 when test strip adaptor 220 is coupled to or integrated with mobile computing device adaptor 210.

In some embodiments, mobile computing device adaptor 210 includes a bottom opening (not shown) optically communicated with top opening 211. In some embodiments, mobile computing device adaptor 210 is coupled to mobile computing device 100 at a position that the bottom opening aligns with both camera 104 and light source area 118.

In some embodiments, light source area 118 is configured to emit light from screen 108. The emitted light passes through the bottom opening and its corresponding top opening 211, enters test strip adaptor 220 through test strip adaptor opening 223 corresponding to top opening 211, and illuminates the reaction area of test strip 221. Camera 104 is configured to capture an image of the reaction area through test strip adaptor opening 223, top opening 211 and the bottom opening. Photometric test strip analyzer 117 is configured to analyze the image to obtain information associated with the analyte.

Figure 3:
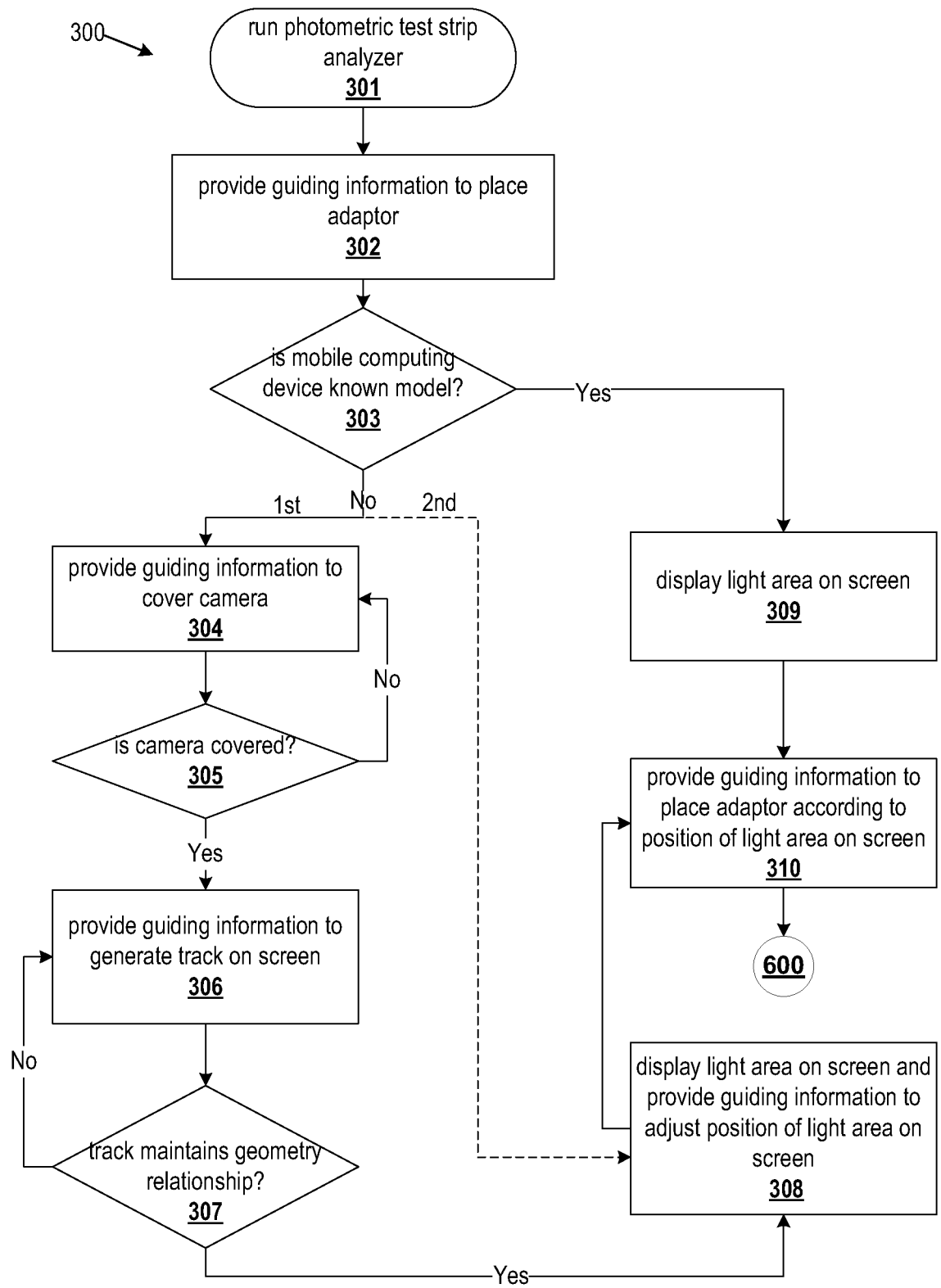
FIG. 3 is a flow chart of method 300 to improve placement of an adaptor to a mobile computing device to measure a test strip coupled to the adaptor with a camera and a screen on a face of the mobile computing device, according to some embodiments of the present disclosure.

FIG. 3 is a flowchart of method 300 to improve placement of an adaptor to a mobile computing device to measure a test strip coupled to the adaptor with a camera and a screen on a face of the mobile computing device, according to some embodiments of the present disclosure. Method 300 may include one or more operations, functions, or actions illustrated by one or more blocks. Although the blocks of method 300 and other methods described herein are illustrated in sequential orders, these blocks may also be performed in parallel, or in a different order than those described herein. Also, the various blocks may be combined into fewer blocks, divided into additional blocks, or eliminated based upon the desired implementation. Method 300 may begin in block 301.

In block 301, processor 112 receives user input to run photometric test strip analyzer 117. In response, processor 112 executes the code for photometric test strip analyzer 117. Block 301 may be followed by block 302.

In block 302, processor 112 provides first guiding information for a user to place mobile computing device adaptor 210 to mobile computing device 100. In some embodiments, the first guiding information may include, but not limited to, information displayed on user interface area 119 or sound outputted by ear speaker 106. The first guiding information may have similar or the same form with other guiding information described in this disclosure. Block 302 may be followed by block 303.

In block 303, processor 112 detects the model of mobile computing device 100 and determines whether the model is a known model based on data stored in volatile memory 114 and/or nonvolatile memory 116 or in a database accessible by processor 112. In response to the detected model of mobile computing device 100 being a known model, block 303 may be followed by block 309. In block 309, a light area (e.g., light area 510 in FIG. 5) is displayed on screen 108 based on position data associated with the known model stored in volatile memory 114 and/or nonvolatile memory 116 or in a database accessible by processor 112. In some embodiments, the light area may correspond to light source area 118. Block 309 may be followed by block 310. In block 310, processor 112 provides second guiding information for a user to place mobile computing device adaptor 210 to mobile computing device 100 according to the position of the light area on screen 108.

In response to the model of mobile computing device 100 not being a known model, in some embodiments, in a first approach (i.e., solid line "1st" in FIG. 3), block 303 may be followed by block 304. In some other embodiments, in a second approach (i.e., dash line "2nd" in FIG. 3), block 303 may be followed by block 308.

In the first approach, in block 304, processor 112 provides third guiding information for a user to cover camera 104. Camera 104 may be covered by a finger of the user or an instrument (e.g., stylus pen) operated by the user. In some other embodiments, screen 108 is configured to illuminate a portion of screen 108 adjacent to camera 104 as an indicator to assist the user to place the finger or the stylus pen. Block 304 may be followed by block 305.

Recently, mobile computing device 100 may include multiple functions and have components corresponding to the functions. These components may look similarly from their appearances. For example, proximity sensor 103 and camera 104 have similar appearances and are adjacent to each other. The user may confuse proximity sensor 103 with camera 104. Therefore, in block 305, processor 112 determines whether camera 104 is covered. In some embodiments, processor 112 issues instructions to camera 104 to capture a plurality of images within a time frame. In response to camera 104 is covered, captured images will have certain characteristics. Some example characteristics may include, but not limited to, color characteristics (e.g., R, G, B characteristics), texture characteristics, the number of positive and negative pixels. In some embodiments, the characteristics in the plurality of captured images are compared to each other for the consistency check purposes. These characteristics are different from the characteristics of images captured by camera 104 when the user mistakenly covering proximity sensor 103 and leaving camera 104 uncovered. In response to processor 112 determines camera 104 is not covered, block 305 may be looped back to block 304. In response to processor 112 determines camera 104 is covered, block 305 may be followed by block 306.

In block 306, processor 112 provides fourth guiding information for a user to generate a track on screen 108. In some embodiments, the track maintains a geometry relationship with screen 108 (e.g., in conjunction with FIG. 1, substantially in parallel to side 105 of screen 108) to align light source area 118 (e.g., light area 510), camera 104 and the key area of the test strip with each other. The details of the alignment of light source area 118, camera 104 and the key area of the test strip will be further described below. In some embodiments, screen 108 is a touch screen which is capable of detecting a track of user's fingertip or a stylus pen. Block 306 may be followed by block 307.

In block 307, processor 112 determines whether the track generated in block 306 maintains the geometry relationship.

Figure 4:
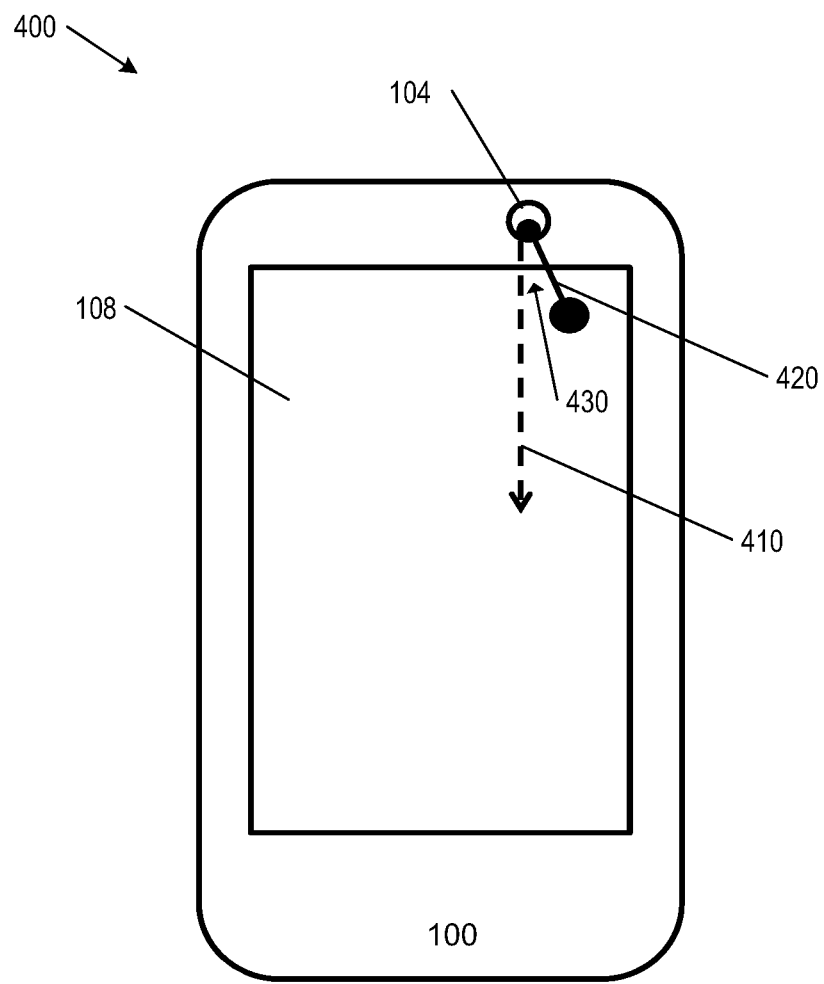
FIG. 4 illustrates a perspective view 400 of mobile computing device 100 showing first track 410 and second track 420 on screen 108 of mobile computing device 100, according to some embodiments of the present disclosure.

Referring to FIG. 4, FIG. 4 illustrates a perspective view 400 of mobile computing device 100 showing first track 410 and second track 420 on screen 108 of mobile computing device 100, according to some embodiments of the disclosure.

In FIG. 4, first track 410 is a track that user's fingertip or stylus pen moves substantially vertically from camera 104 to screen 108, which is substantially in parallel to side 105 of screen 108. Second track 420 is a track that deviates from first track 410 with angle 430. In some embodiments, angle 430 may between about 0.1 degrees to about 20 degrees (e.g., about 5 degrees).

Referring back to FIG. 3, in block 307 and in conjunction with FIG. 4, in response to the detected track is first track 410 or between first track 410 and second track 420, processor 112 determines the track maintains the geometry relationship and block 307 may be followed by block 308. Otherwise, block 307 may loop back to block 306.

Figure 5:
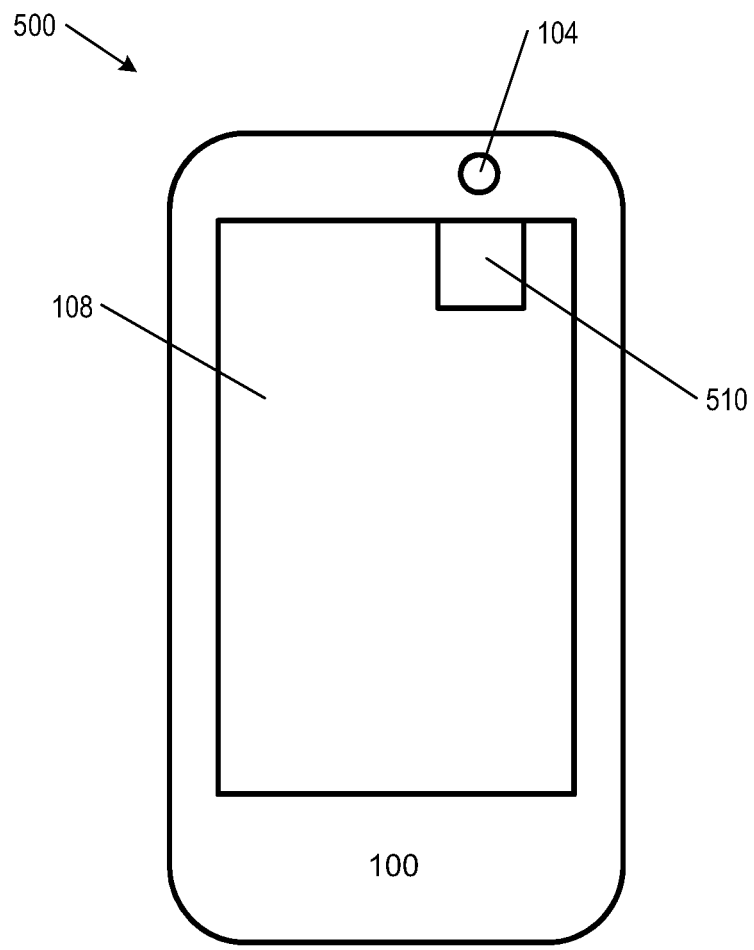
FIG. 5 illustrates a perspective view 500 of mobile computing device 100 showing light area 510 on screen 108 of mobile computing device 100, according to some embodiments of the present disclosure.

Referring to FIG. 5, FIG. 5 illustrates a perspective view 500 of mobile computing device 100 showing light area 510 on screen 108 of mobile computing device 100, according to some embodiments of the present disclosure.

In conjunction with FIG. 3 and FIG. 5, in block 308, processor 122 configures screen 108 to display light area 510 on screen 108 based on the track being determined to maintain a geometry relationship in block 307. In addition, in block 308, processor 112 provides fifth guiding information for the user to adjust the position of light area 510 on screen 108. For example, the user may touch, hold and move light area 510 to a new position on screen 108, which is more aligned to camera 104 than light area 510 before being moved. Screen 108 is configured to track user's fingertip or stylus pen to illuminate screen 108 accordingly and move light area 510 on screen 108. In some embodiments, light area 510 may correspond to light source area 118.

As set forth above, in the second approach, block 303 may be followed by block 308 without going through blocks 304 to 307.

In some embodiments, in response to the user stop adjusting the position of light area 510, processor 112 is configured to associate the position of light area 510 with the model of mobile computing device 100 and categorize the model of mobile computing device 100 as a known model for future use. The association and categorization information of light area 510 and the model of mobile computing device 10 may be uploaded to a database. The database may be accessed by multiple users. In some embodiments, photometric test strip analyzer 117 on other device of other users may be upgraded through wired or wireless connections to the database and retrieves the association and categorization information of light area 510 and the model of mobile computing device 10 from the database. Over time, the number of the models of mobile computing device 100 will be increased, which may lead a more user friendly experience (e.g., from block 303 to block 309 in FIG. 3).

In block 310, processor 112 provides sixth guiding information for the user to place mobile computing device adaptor 210 to mobile computing device 100 according to the position of the light area 510 on screen 108. In some embodiments, block 310 may be followed by method 600 to improve measurement of the analyte.

Figure 6:
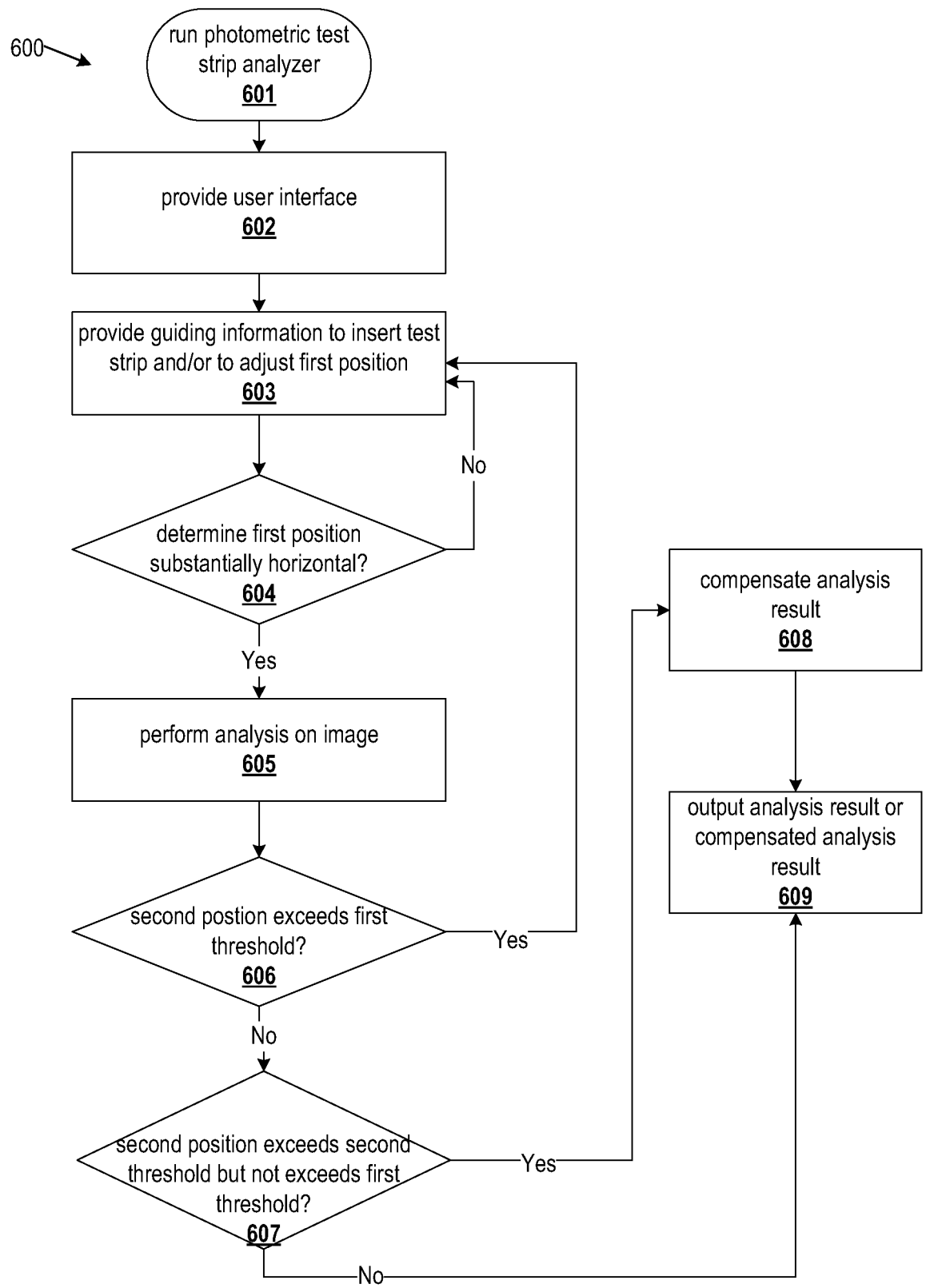
FIG. 6 is a flowchart of method 600 to improve measurement of an analyte with a mobile computing device coupled to an adaptor configured to receive a test strip having a key area containing a reagent that reacts with the analyte, according to some embodiments of the present disclosure.

FIG. 6 is a flowchart of method 600 to improve measurement of an analyte with mobile computing device 100 coupled to an adaptor (e.g., mobile device adaptor 210 or integrated mobile device adaptor 210 and test strip adaptor 220) configured to receive test strip 221, according to some embodiments of the present disclosure. Method 600 may include one or more operations, functions, or actions illustrated by one or more blocks. Although the blocks of method 600 and other methods described herein are illustrated in sequential orders, these blocks may also be performed in parallel, or in a different order than those described herein. Also, the various blocks may be combined into fewer blocks, divided into additional blocks, or eliminated based upon the desired implementation. Method 600 may begin in block 601.

In block 601, in conjunction with FIG. 1, processor 112 receives user input to run photometric test strip analyzer 117. In response processor 112 executes the code of photometric test strip analyzer 117. Block 601 may be followed by block 602.

In block 602, processor 112 provides an user interface on screen 118 to interact with the user. Block 602 may be followed by block 603.

In block 603, processor 112 provides first guiding information for a user to insert test strip 221 into test strip adaptor 220 and/or to adjust a first position of mobile computing device 100.

In conjunction with FIG. 2, the user may insert test strip 221 into test strip adaptor 220, which is coupled to or integrated with mobile computing device adaptor 210. In some embodiments, mobile computing device 100 maintains a substantially horizontal position for light source area 118 emitting light to illuminate the reaction area of test strip 221, for camera 104 capturing images of the reaction area, and for processor 112 (in FIG. 1) to execute codes of photometric test strip analyzer 117 (in FIG. 1) to analyze the captured images of the reaction area.

Figure 7:
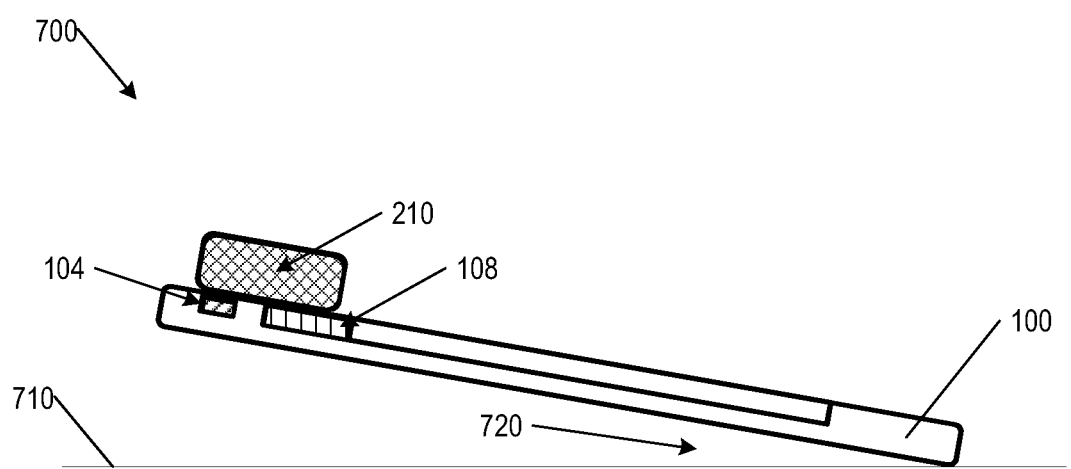
FIG. 7 illustrates a perspective view 700 of mobile computing device 100 showing a position of mobile computing device 100, according to some embodiments of the present disclosure.

Referring to FIG. 7, FIG. 7 illustrates a perspective view 700 of mobile computing device 100 showing a position of mobile computing device 100, according to some embodiments of the present disclosure. In some embodiments, in conjunction with FIG. 6 and in block 603, processor 112 provides second guiding information for the user to adjust the first position of mobile computing device 100 to a substantially horizontal position, which is substantially in parallel to referenced horizontal surface 710. In some embodiments, angle 720 is less than a threshold when mobile computing device 100 is disposed substantially in parallel to referenced horizontal surface 710. In some embodiments, the analysis accuracy of the captured images is increased in response to disposing mobile computing device 100 substantially in parallel to referenced horizontal surface 710. Block 603 may be followed by block 604.

In block 604, in conjunction with FIG. 7, processor 112 detects the first position of mobile computing device 100 and determines whether the first position of mobile computing device 100 is substantially horizontal (e.g., in parallel to horizontal reference surface 710). In some embodiments, processor 112 accesses data collected by a gyroscope sensor and/or an accelerometer sensor embedded in or attached on mobile computing device 100 to obtain angle 720. In response to angle 720 exceeds a first threshold, block 604 may loop back to block 603 to provide second guiding information for the user to adjust the first position of mobile computing device 100 to be substantially in parallel to horizontal reference surface 710. In response to angle 720 does not exceed the first threshold, block 604 may be followed by block 605.

In block 605, processor 112 executes the code of photometric test strip analyzer 117 to capture images of the reaction area of test strip 221 with camera 104 and then perform an analysis on the images to obtain information associated with the analyte. Block 605 may be followed by block 606.

In block 606, processor 112 detects a second position of mobile computing device 100 during the analysis on the images captured by camera 104 and determines whether the second position is substantially horizontal (e.g., in parallel to horizontal reference surface 710).

As set forth above, processor 112 accesses data collected by a gyroscope sensor and/or an accelerometer sensor embedded in or attached on mobile computing device 100 to obtain angle 720 during the analysis on the images captured by camera 104. In response to angle 720 exceeds the first threshold, block 606 may loop back to block 603 to terminate the analysis and provide second guiding information for the user to adjust the position of mobile computing device 100 to be substantially in parallel to horizontal reference surface 710. In response to angle 720 does not exceed the first threshold, block 606 may be followed by block 607.

In block 607, in response to angle 720 exceeds a second threshold but does not exceed the first threshold, block 607 may be followed by block 608. In response to angle 720 does not exceed the second threshold, block 607 may be followed by block 609 to output the analysis result (e.g., information associated with the analyte).

In block 608, processor 112 is configured to retrieve historical data corresponding to angle 720, which exceeds the second threshold but does not exceed the first threshold. The historical data may include compensation values corresponding to various angles 720 between the first threshold and the second threshold. In some embodiments, based on angle 720 detected in block 606, processor 112 may obtain a compensation value based on the historical data through interpolation or looking up. Photometric test strip analyzer 117 may utilize the compensation value to compensate the analysis result. Block 608 may be followed by block 609 to output the compensated analysis result.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

We claim:

1. A method to improve placement of an adaptor to a mobile computing device to measure a test strip coupled to the adaptor with a camera and a screen on a face of the mobile computing device, the method comprising:
   determining whether a model of the mobile computing device is a first known model based on stored data accessible by the mobile computing device;
   in response to a determination that the model is not the first known model:
   guiding a user to generate a track from the camera to the screen;
   displaying a light area on a first portion of the screen based on the track;
   guiding the user to move the light area to a position on the screen aligned with the camera, wherein the light area and the camera are aligned with a key area of the test strip so that the camera is configured to capture an image of the key area; and
   guiding the user to place the adaptor to the mobile computing device according to the position of the light area on the screen.

2. The method of claim 1, wherein the first portion is configured as a light source to illuminate the key area of the test strip.

3. The method of claim 1, further comprising guiding the user to cover the camera.

4. The method of claim 3, wherein guiding the user to generate the track from the camera to the screen is in response to determining that the camera is covered.

5. The method of claim 4, wherein the track maintains a geometry relationship with the screen.

6. The method of claim 4, further comprising detecting the track on the screen.

7. The method of claim 6, further comprising, in response to the detected track being within a predetermined range on the screen, displaying the light area on the first portion of the screen based on the detected track.

8. The method of claim 7, further comprising guiding the user to move the light area on the screen so that the light area aligns with the camera.

9. The method of claim 1, further comprising:
   after the determination that the model of the mobile computing device is not the first known model:
   associating the position of the light area with the model of the mobile computing device;
   categorizing the model of the mobile computing device to be a second known model; and
   storing the second known model in a database accessible by the mobile computing device.

* * * * *